United States Patent [19]

Eidenschink et al.

[11] Patent Number: 4,551,264
[45] Date of Patent: Nov. 5, 1985

[54] POLYHALOGENOAROMATIC COMPOUNDS FOR LIQUID CRYSTAL COMPOSITIONS

[75] Inventors: Rudolf Eidenschink, Dieburg; Michael Römer, Rodgau; Georg Weber, Erzhausen, all of Fed. Rep. of Germany

[73] Assignee: Merck Patent Gesellschaft mit beschränkter Haftung, Darmstadt, Fed. Rep. of Germany

[21] Appl. No.: 474,862

[22] Filed: Mar. 14, 1983

[30] Foreign Application Priority Data

Mar. 13, 1982 [DE] Fed. Rep. of Germany ....... 3209178

[51] Int. Cl.$^4$ .......................... C09K 3/34; C02F 1/13;
C07C 121/75; C07C 79/12; C07C 49/813;
C07C 87/60; C07C 43/225; C07C 69/157;
C07C 69/773; C07D 319/06

[52] U.S. Cl. ................................. 252/299.62; 560/73;
560/85; 252/299.61; 560/102; 560/107;
252/299.63; 564/306; 564/307; 252/299.64;
564/441; 564/442; 252/299.65; 568/325;
252/299.66; 568/329; 568/642; 350/350 R;
568/643; 568/647; 350/350 S; 568/707;
568/743; 260/465 D; 568/928; 568/585;
260/465 F; 568/631; 568/644; 260/465 G;
568/645; 568/709; 549/370; 568/746; 568/931;
549/374; 570/129; 549/369; 570/182; 549/373;
570/186; 570/188; 549/371; 549/375; 560/20;
560/21; 560/48; 560/49; 560/59; 560/61;
560/62; 560/1; 560/83; 560/84; 560/43;
560/47; 560/51; 560/53; 560/65; 560/72

[58] Field of Search .................. 252/299.61, 299.62,
252/299.63, 299.64, 299.66, 299.5; 250/350 R,
350 S; 260/465 D, 465 F, 465 G; 549/370, 371,
374, 375, 369, 373; 560/20, 21, 43, 47, 48, 49,
51, 53, 59, 61, 62, 65, 72, 73, 84, 85, 102, 107, 1;
568/325, 329, 709, 585, 631, 642, 643, 644, 645,
647, 707, 746, 743, 928, 931; 570/129, 182, 186,
188; 564/306, 307, 441, 442

[56] References Cited

U.S. PATENT DOCUMENTS

| | | | |
|---|---|---|---|
| 3,974,087 | 8/1976 | Gray et al. | 252/299.66 |
| 4,151,302 | 4/1979 | Gante et al. | 424/317 |
| 4,216,109 | 8/1980 | Mizukuchi | 252/299.65 |
| 4,256,656 | 2/1981 | Beguin et al. | 252/299.62 |
| 4,368,135 | 1/1983 | Osman | 252/299.63 |
| 4,400,061 | 8/1983 | Carr et al. | 252/299.62 |
| 4,400,293 | 8/1983 | Romer et al. | 252/299.63 |
| 4,405,488 | 9/1983 | Sugimori et al. | 252/299.63 |
| 4,415,470 | 11/1983 | Eidenschink et al. | 252/299.63 |
| 4,419,264 | 12/1983 | Eidenschink et al. | 252/299.5 |
| 4,478,740 | 10/1984 | Eidenschink et al. | 252/299.63 |
| 4,479,885 | 10/1984 | Mukoh et al. | 252/299.62 |
| 4,490,305 | 12/1984 | Eidenschink et al. | 252/299.5 |
| 4,505,838 | 3/1985 | Romer et al. | 252/299.63 |

FOREIGN PATENT DOCUMENTS

| | | | |
|---|---|---|---|
| 0019665 | 5/1979 | European Pat. Off. | 252/299.63 |
| 84194 | 7/1983 | European Pat. Off. | 252/299.61 |
| 2356085 | 5/1974 | Fed. Rep. of Germany | 252/299.66 |
| 2933563 | 2/1981 | Fed. Rep. of Germany | 252/299.63 |
| 2939782 | 4/1981 | Fed. Rep. of Germany | 252/299.64 |
| 3208089 | 9/1983 | Fed. Rep. of Germany | 252/299.63 |
| 3317921 | 12/1983 | Fed. Rep. of Germany | 252/299.63 |
| 57-179134 | 11/1982 | Japan | 252/299.63 |
| 58-13542 | 1/1983 | Japan | 252/299.63 |
| 58-23634 | 2/1983 | Japan | 252/299.63 |
| 58-18326 | 2/1983 | Japan | 252/299.63 |
| 58-150542 | 9/1983 | Japan | 252/299.63 |
| 58-148839 | 9/1983 | Japan | 252/299.67 |
| 58-188840 | 11/1983 | Japan | 252/299.63 |
| 58-188839 | 11/1983 | Japan | 252/299.63 |
| 2039937 | 8/1980 | United Kingdom | 252/299.66 |
| 2063250 | 6/1981 | United Kingdom | 252/299.63 |
| 2063287 | 6/1981 | United Kingdom | 252/299.63 |

OTHER PUBLICATIONS

Beguin, A. et al., J. de Physique, Coll. C3, Suppl. No. 4, Tome 40, pp. C3-9-14, (Apr. 1979).
Sirutkaitis, R. et al., Advances in Liq. Cryst. Res. and Appl., Bata, L., Pergamon Press, Oxford, pp. 1023–1028, (1980).
Gray, G. W. et al., Mol. Cryst. Liq. Cryst., vol. 67, No. 1–4, pp. 1–24, (1981).

*Primary Examiner*—Teddy S. Gron
*Attorney, Agent, or Firm*—Millen & White

[57] ABSTRACT

New polyhalogenoaromatic compounds of Formula I

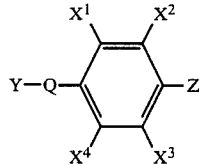

wherein
Y and Z are each independently alkyl, alkoxy or alkanoyl each of 1 to 12 C atoms, —COOR$^1$, —O—CO—R$^1$, CN, NO$_2$, NH$_2$ or OH;
Q is one or two identical or different radicals selected from Ph, Cy, 1,4-bicyclo[2,2,2]octylene or 1,3-dioxane-2,5-diyl;
X$^1$ to X$^4$ are each independently H, F, Cl or Br;
R$^1$ is alkyl of 1 to 4 C atoms, Ph—R$^2$ or Cy—R$^2$;
R$^2$ is alkyl or alkoxy each of 1–12 C atoms or CN;
Ph is 1,4-phenylene; and Cy is 1,4-cyclohexylene,
can be used as components of liquid-crystal dielectrics.

21 Claims, No Drawings

POLYHALOGENOAROMATIC COMPOUNDS FOR LIQUID CRYSTAL COMPOSITIONS

The present invention relates to new polyhalogenoaromatic compounds.

SUMMARY OF THE INVENTION

It is an object of the present invention to provide new liquid-crystal compounds suitable for use as components of liquid-crystal dielectrics.

Upon further study of the specification and appended claims, further objects and advantages of this invention will become apparent to those skilled in the art.

These objects have been achieved by providing new polyhalogenoaromatic compounds of Formula I $$Y-Q-\underset{X^4\quad X^3}{\overset{X^1\quad X^2}{\bigcirc}}-Z \qquad \text{I}$$

wherein Y and Z are each independently alkyl, alkoxy or alkanoyl each of 1 to 12 C atoms, $-COOR^1$, $-O-CO-R^1$, CN, $NO_2$, $NH_2$ or OH; Q is one or two, identical or different, groups selected from Ph, Cy, 1,4-bicyclo[2,2,2]octylene or 1,3-dioxane-2,5-diyl; $X^1$ to $X^4$ are each independently H, F, Cl or Br; $R^1$ is alkyl of 1 to 4 C atoms, $Ph-R^2$ or $Cy-R^2$; $R^2$ is alkyl or alkoxy each of 1–12 C atoms, or CN; Ph is 1,4-phenylene and Cy is 1,4-cyclohexylene; with the proviso that not more than one of $X^1$ and $X^2$ and not more than one of $X^3$ and $X^4$ is a hydrogen atom.

Like similar compounds, for example those known from European Laid-Open Specification No. 0,019,665, these substances can be used as components of liquid-crystal dielectrics, particularly for displays based on the principle of the twisted cell, the guest-host effect, the effect of the deformation of aligned phases or the effect of dynamic scattering.

This invention also relates to the use of the compounds of Formula I as components of liquid-crystal dielectrics, to liquid-crystal dielectrics containing at least one compound of Formula I and to electrooptical display elements containing dielectrics of this type.

DETAILED DISCUSSION

It has been found that the compounds of Formula I are excellently suitable for use as components of liquid-crystal dielectrics. In particular, they permit a considerable latitude of variation in the dielectric anisotropy and in the optical anisotropy. Furthermore, they exhibit high average dielectric constant values and thus a high dissolving power for conducting salts and for dichroic dyestuffs.

In the pure state, the compounds of Formula I are colorless and form liquid-crystalline mesophases in a temperature range which is favorably placed for electrooptical use.

Compounds of Formula I which are optically active are suitable as chiral doping substances for the preparation of cholesteric phases such as can be used for White-Taylor dye cells.

The present invention therefore relates to the compounds of Formula I and to a process for their preparation, comprising reacting a compound of Formula II $$\underset{X^4\quad X^3}{\overset{X^1\quad X^2}{\bigcirc}}-Z' \qquad \text{II}$$

wherein Z' is CN or $NO_2$ and $X^1$ to $X^4$ are as defined for Formula I with a reactive derivative of a percarboxylic acid of Formula III $$Y-Q-CO_3H \qquad \text{III}$$

wherein Y and Q are as defined for Formula I, and, optionally, converting radical Z' in a resulting compound of Formula I (Z=Z') into an alkyl, alkoxy or alkanoyl group having 1–12 C atoms in each case or into an $NH_2$, OH, $COOR^1$ or $-O-CO-R^1$ group.

In the preceding and following text, Y, Z, Q, $X^1$ to $X^4$, $R^1$, $R^2$, Ph, Cy and Z' are as defined above, unless anything contrary is expressly indicated.

The compounds of Formula I embrace compounds of the following partial Formulae Ia to It:

| | |
|---|---|
| Y—Ph—W—Z | Ia |
| Y—Cy—W—Z | Ib |
| Y—Bi—W—Z | Ic |
| Y—Dio—W—Z | Id |
| Y—Ph—Ph—W—Z | Ie |
| Y—Ph—Cy—W—Z | If |
| Y—Ph—Bi—W—Z | Ig |
| Y—Ph—Dio—W—Z | Ih |
| Y—Cy—Ph—W—Z | Ii |
| Y—Cy—Cy—W—Z | Ij |
| Y—Cy—Bi—W—Z | Ik |
| Y—Cy—Dio—W—Z | Il |
| Y—Bi—Ph—W—Z | Im |
| Y—Bi—Cy—W—Z | In |
| Y—Bi—Bi—W—Z | Io |
| Y—Bi—Dio—W—Z | Ip |
| Y—Dio—Ph—W—Z | Iq |
| Y—Dio—Cy—W—Z | Ir |
| Y—Dio—Bi—W—Z | Is |
| Y—Dio—Dio—W—Z | It | wherein, for the sake of brevity, W is $2-X^2-3-X^1-5-X^4-6-X^3-1,4$-phenylene, Bi is 1,4-bicyclo-[2,2,2]octylene and Dio is 1,3-dioxane-2,5-diyl.

The compounds of Formula Ib, and also those of Formulae Ia, Ic, Ie, If, Ii and Ij, are preferred.

In the compounds of the Formula I, and also Ib, Id, If, Ih to Il, In and Ip to It, preferred stereoisomers are those in which the two substituents on the cyclohexylene radicals and the dioxanediyl radicals are each in the trans-position relative to one another.

The alkyl, alkoxy and alkanoyl groups in the compounds of the Formula I, and also Ia to It, are preferably linear. Alkyl is preferably ethyl, n-propyl, n-butyl, n-pentyl or n-hexyl, and also, preferably, methyl, n-heptyl, n-octyl, n-nonyl, n-decyl, n-undecyl or n-dodecyl. Alkoxy is preferably methoxy, ethoxy, n-propoxy, n-butoxy, n-pentoxy or n-hexoxy and also, preferably, n-heptoxy, n-octoxy, n-nonoxy, n-decyloxy, n-undecyloxy or n-dodecyloxy. Alkanoyl is preferably acetyl, propionyl, butyryl, valeryl or hexanoyl and also, preferably, formyl, heptanoyl, octanoyl, nonanoyl, decanoyl, undecanoyl or dodecanoyl.

Compounds of Formula I, and also Ia to It, containing branched alkyl, alkoxy or alkanoyl groups can occasionally be of importance because of better solubility in the customary liquid-crystal base materials, but are of importance particularly as chiral doping substances, if they are optically active. Branched groups of this type as a rule do not contain more than one chain branching. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-heptyl (=1-methylhexyl) or 2-octyl (=1-methylheptyl); preferred branched alkoxy radicals are isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy; preferred branched alkanoyl radicals are isobutyryl, 2-methylbutyryl, 3-methylbutyryl, 2-methylpentanoyl, 3-methylpentanoyl and 2-ethylhexanoyl.

Specifically, Y is preferably alkyl and Z is preferably CN or $NO_2$.

The radical W can preferably be 2,6-dihalogeno-1,4-phenylene and also 2,5-dihalogeno-1,4-phenylene, 3,5-dihalogeno-1,4-phenylene, 2,3,5-trihalogeno-1,4-phenylene, 2,3,6-trihalogeno-1,4-phenylene or 2,3,5,6-tetrahalogeno-1,4-phenylene, halogeno being preferably F and also Cl or Br. W is especially 2,6-difluoro-1,4-phenylene, 2-chloro-6-fluoro-1,4-phenylene or 2,6-dichloro-1,4-phenylene.

$R^1$ is preferably linear alkyl of 1-4 C atoms, Ph—$R^2$ or Cy—$R^2$.

$R^2$ is preferably alkyl especially of 3, 4 or 5 C atoms; in the group Ph—$R^2$, $R^2$ is, in addition, preferably alkoxy especially of 1, 2, 3, 4 or 5 C atoms or CN.

The compounds of Formula I are, moreover, prepared by methods which are in themselves known, such as are described in the literature (for example in the standard works, such as Houben-Weyl, Methoden der Organischen Chemie (Methods of Organic Chemistry), Georg-Thieme-Verlag, Stuttgart), specifically under reaction conditions which are known and suitable for the reactions mentioned. In this connection it is also possible to make use of variants which are in themselves known but are not mentioned here in greater detail.

The starting materials can, if desired, also be formed in situ, in such a manner that they are not isolated from the reaction mixture, but are immediately reacted further to give the compounds of Formula I.

The compounds of the Formula I can be prepared by first reacting a benzonitrile derivative (preferably 2,6-difluorobenzonitrile, 2-chloro-6-fluorobenzonitrile or 2,6-dichlorobenzonitrile) or a nitrobenzene derivative (preferably 2,6-difluoronitrobenzene, 2-chloro-6-fluoronitrobenzene or 2,6-dichloronitrobenzene) of Formula II with a reactive derivative of a percarboxylic acid of Formula III (preferably with an ester of the formula Y—Q—$CO_3$alkyl, which can be formed in situ from the corresponding acid chloride of the formula Y—Q—COCl and the corresponding alkyl hydroperoxide and in which the alkyl group contains, in particular, 1-6 C atoms, but is preferably tert-butyl; or with a diacyl peroxide of the formula Y—Q—CO—O—O—CO—Q—Y).

This reaction is preferably carried out in the presence of an inert solvent, for example benzene, in general at temperatures of about 0° to about 150°, preferably 60° to 110°. If the pre-ester is formed in situ from the acid chloride, it is advisable to add a base, such as pyridine or triethylamine in order to neutralize the hydrogen chloride formed.

The starting materials of Formulae II and III and their reactive derivatives are for the most part known; in all cases they can be prepared conventionally without difficulty by standard processes of organic chemistry from compounds known from the literature.

If desired, the CN group or the $NO_2$ group in the product thus obtained of Formula I (Z=Z') can be converted into another radical Z.

Thus it is possible, for example, to react a resulting nitrile (I, Z=CN) with an organometallic compound of the formula R—M (wherein R is alkyl of 1-11 C atoms and M is MgCl, MgBr, MgI or Li) to give the corresponding ketone (I, Z=alkanoyl having 2-12 C atoms), preferably under the customary conditions of a Grignard reaction or of a reaction with organo-Li compounds in an inert solvent, for example an ether, such as diethyl ether, diisopropyl ether or tetrahydrofuran, or a hydrocarbon, such as benzene, or a mixture of solvents of this type, at temperatures of about 0° to 80°. The mixture is then hydrolyzed, preferably in an aqueous acid medium, for example by means of hydrochloric acid, sulfuric acid or $NH_4Cl$, at temperatures of about 0° to about 120°.

Aldehydes of Formula I (Z=CHO) are obtainable, for example, from the nitriles (I, Z=CN) by means of $LiAlH(OC_2H_5)_3$ or $NaAlH(OC_2H_5)_3$ in diethyl ether or tetrahydrofuran or by means of $SnCl_2/HCl$ in diethyl ether using Stephen's method.

Compounds of Formula I wherein Z is an alkyl group are obtainable, for example, by reducing the ketones (I, Z=alkanoyl) using Clemmensen's methods (by means of zinc, amalgamated zinc or tin and hydrochloric acid, preferably in an aqueous-alcoholic solution or in a heterogeneous phase containing water/benzene or water/toluene at temperatures of about 80° to 120°) or of Wolff-Kishner (by means of hydrazine, preferably in the presence of an alkali, such as KOH or NaOH, in a high-boiling solvent, such as diethylene glycol or triethylene glycol at temperatures of about 100° to 200°).

Amines (I, Z=$NH_2$) can be prepared by reducing the nitro compounds (I, Z=$NO_2$), for example by hydrogenation over a metal carrier catalyst, such as Pt, Pd or Raney Ni, which can also be present in the form of an oxide (for example $PtO_2$) or on a support (for example Pd-on-charcoal, Pd/$CaCO_3$ or Pd/$SrCO_3$) in an inert solvent, such as methanol, ethanol, isopropanol, ethyl acetate, tetrahydrofuran, dioxane or acetic acid, at temperatures of about 20° to 100° and under pressures of about 1 to 200 bar, or by a chemical route, for example by means of nascent hydrogen, which can be produced using the systems Fe/HCl, Zn/NaOH, Zn/$CH_3COOH$ or Sn/HCl, or by means of $SnCl_2/HCl$, $H_2S$ or sulfides or $Na_2S_2O_4$.

Phenols (I, Z=OH) are obtainable, for example, by diazotizing the amines (I, Z=$NH_2$) and subsequent decomposition by boiling. Diazotization can be carried out in a customary manner using a salt or an ester of nitrous acid (such as $NaNO_2$ or butyl nitrite) in an aqueous acid medium, and the resulting diazonium salt solution can then be decomposed by hydrolysis at temperatures of about 50° to 100°.

Alkoxy compounds (I, Z=alkoxy) are obtainable by alkylating the phenols (I, Z=OH), the phenol being preferably first converted into a phenate, for example being converted into the corresponding alkali metal phenate by treatment with NaOH, KOH, Na₂CO₃ or K₂CO₃. This phenate can then be reacted with the corresponding alkyl halide or sulfonate or dialkyl sulfate, preferably in an inert solvent, such as acetone, dimethylformamide or dimethyl sulfoxide, or an excess of aqueous or aqueous-alcoholic NaOH or KOH at temperatures of about 20° to 100°.

Acylating the phenols (I, Z=OH) or their reactive derivatives with carboxylic acids of the formula R¹—COOH or reactive derivatives of the latter leads to the corresponding esters (I, Z=—O—CO—R¹). Esters of the Formula I (Z=COOR¹) are obtainable by hydrolyzing the nitriles (I, Z=CH) to give the corresponding carboxylic acids (I, Z=COOH), for example in an alkaline medium by means of aqueous alcoholic alkali at temperatures of about 20° to about 100°, and subsequently reacting these carboxylic acids or their reactive derivatives with alcohols or phenols of the formula R¹OH or with reactive derivatives thereof.

Suitable reactive derivatives of the carboxylic acids of Formula I (Z=COOH) or R¹—COOH include in particular, the acid halides, above all the chlorides and bromides, and also the anhydrides and azides. Suitable reactive derivatives of the phenols of Formula I (Z=OH) or of the alcohols of the formula R¹—OH include, in particular, the corresponding metal phenates, for example sodium phenate or potassium phenate, or metal alcoholates.

The esterification is advantageously carried out in the presence of an inert solvent. Suitable solvents include, in particular, ethers, e.g., diethyl ether, di-n-butyl ether, tetrahydrofuran, dioxane or anisole, ketones, e.g. acetone, butanone or cyclohexanone, amides, e.g. dimethylformamide or phosphoric acid hexamethyltriamide, hydrocarbons, e.g. benzene, toluene or xylene, halogenated hydrocarbons, e.g. carbon tetrachloride or tetrachloroethylene, and sulfoxides, e.g. dimethyl sulfoxide or sulfolane. Water-immiscible solvents can advantageously be used at the same time in order to remove by azeotropic distillation the water formed in the esterification. When suitable, it is also possible to use an excess of an organic base, for example pyridine, quinoline or triethylamine, as the solvent for the esterification. The esterification can also be carried out in the absence of a solvent, for example by simply heating the components in the presence of sodium acetate.

The reaction temperature is usually −50° to +250°, preferably −20° to +80°. At these temperatures the esterification reactions are, as a rule, complete after 15 minutes to 48 hours.

In an individual case, the reaction conditions for the esterification depend largely on the nature of the starting materials used. Thus a free carboxylic acid of Formula II is as a rule reacted with an alcohol or phenol of Formula III in the presence of a strong acid, for example a mineral acid, such as hydrochloric acid or sulfuric acid.

A preferred reaction procedure is to react an acid anhydride or, especially, an acid chloride with the phenol or alcohol, preferably in a basic medium, bases of importance being, in particular, alkali metal hydroxides, e.g. sodium hydroxide or potassium hydroxide, alkali metal carbonates or bicarbonates, e.g. sodium carbonate, sodium bicarbonate, potassium carbonate or potassium bicarbonate, alkali metal acetates, e.g. sodium acetate or potassium acetate, alkaline earth metal hydroxides, e.g. calcium hydroxide, or organic bases, e.g. triethylamine, pyridine, lutidine, collidine or quinoline.

The dielectrics of this invention comprise 2 to 15, preferably 3 to 12 components, including at least one compound of Formula I. The other constituents are preferably selected from the nematic or nematogenic substances, in particular the known substances, belonging to the classes comprising azoxybenzenes, benzylideneanilines, biphenyls, terphenyls, phenyl or cyclohexylbenzoates, phenyl or cyclohexyl cyclohexanecarboxylates, phenylcyclohexane, cyclohexylbiphenyls, cyclohexylcyclohexanes, cyclohexylnaphthalenes, 1,4-bis-cyclohexylbenzenes, 4,4'-bis-cyclohexylbiphenyls, phenylpyrimidines or cyclohexylpyrimidines, phenyldioxanes or cyclohexyldioxanes, optionally halogenated stilbenes, benzyl phenyl ethers, tolanes and substituted cinnamic acids. The most important compounds which are suitable as constituents of liquid crystal dielectrics of this type can be characterized by Formula IV

$$R^3-A-G-E-R^4 \qquad IV$$

wherein A and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydronaphthalene and tetrahydronaphthalene, quinazoline and tetrahydroquinazoline; G is —CH=CH—, —N(O)=N—, —CH=CL—, —CH=N(O)—, —C≡C—, —CH₂—CH₂—, —CO—O—, —CH₂—O—, —CO—S—, —CH₂—S—, —CH=N—, —COO—Ph—COO—, or a C—C single bond; L is halogen, preferably chlorine, or CN; and R³ and R⁴ are alkyl, alkoxy, alkanoyloxy or alkoxycarbonyloxy each of up to 18, preferably up to 8, carbon atoms, or one of these radicals is also CN, NC, NO₂, CF₃, F, Cl or Br. In most of these compounds R³ and R⁴ are different from one another, one of these radicals being in most cases an alkyl or alkoxy group. Many substances of this type or mixtures thereof are commercially available.

The dielectrics according to this invention contain about 0.1 to 30, preferably 2 to 25, % of one or more compounds of Formula I.

The dielectrics according to this invention are prepared in a manner which is in itself customary. As a rule, the components are dissolved in one another, preferably at elevated temperature. If, in so doing, a temperature above the clear point of the major constituent is selected, the completeness of the dissolution process can be observed particularly easily.

By means of suitable additives it is possible to modify the liquid-crystal dielectrics according to this invention in such a way that they can be used in any hitherto disclosed type of liquid-crystal display element. Additives of this type are familiar to those skilled in the art and are described in detail in the literature. For example, it is possible to add dichroic dyestuffs or substances for modifying the dielectric anisotropy, the viscosity, the conductivity and/or the alignment of the nematic phases. Substances of this type are described, for example, in German Offenlegungschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsover. In the following examples and in the preceding text, all temperatures are set forth uncorrected in degrees Celsius and all parts and percentages are by weight, unless otherwise indicated.

In the examples, M is the melting point and C is the clear point of a liquid crystal substance.

"Working up in the usual manner" means the following: if necessary, water and/or an organic solvent, such as toluene, $CH_2Cl_2$ or $CHCl_3$, is added; the phases are separated, the organic phase is evaporated; and the residue is purified by chromatography (silica gel) and/or crystallization.

EXAMPLE 1

9 g of tert-butyl hydroperoxide and 7.9 g of pyridine are added at 10° to a solution of 21.7 g of trans-4-pentyl-cyclohexanecarboxylic acid chloride in 100 ml of benzene. After stirring at 10° for one hour, the pyridine hydrochloride formed is filtered off and 13.9 g of 2,6-difluorobenzonitrile is added to the solution of the resulting per-ester. After boiling for 16 hours, cooling, washing with water and evaporating, the product is purified by chromatography (silica gel and toluene) to give 2,6-difluoro-4-(trans-4-pentylcyclohexyl)-benzonitrile, M 15°, C 0°.

The following are obtained analogously from the corresponding acid chlorides and the corresponding benzonitriles or nitrobenzenes:

2,5-difluoro-4-(trans-4-pentylcyclohexyl)-benzonitrile
2,6-difluoro-4-(trans-4-methylcyclohexyl)-benzonitrile
2,6-difluoro-4-(trans-4-ethylcyclohexyl)-benzonitrile
2,6-difluoro-4-(trans-4-propylcyclohexyl)-benzonitrile
2,6-difluoro-4-(trans-4-butylcyclohexyl)-benzonitrile
2,6-difluoro-4-(trans-4-hexylcyclohexyl)-benzonitrile
2,6-difluoro-4-(trans-4-heptylcyclohexyl)-benzonitrile
2,6-difluoro-4-(trans-4-dodecylcyclohexyl)-benzonitrile
3,5-difluoro-4-(trans-4-pentylcyclohexyl)-benzonitrile
2-chloro-6-fluoro-4-(trans-4-methylcyclohexyl)-benzonitrile
2-chloro-6-fluoro-4-(trans-4-methylcyclohexyl)-benzonitrile
2-chloro-6-fluoro-4-(trans-4-ethylcyclohexyl)-benzonitrile
2-chloro-6-fluoro-4-(trans-4-propylcyclohexyl)-benzonitrile
2-chloro-6-fluoro-4-(trans-4-butylcyclohexyl)-benzonitrile
2-chloro-6-fluoro-4-(trans-4-pentylcyclohexyl)-benzonitrile
2-chloro-6-fluoro-4-(trans-4-hexylcyclohexyl)-benzonitrile
2-chloro-6-fluoro-4-(trans-4-heptylcyclohexyl)-benzonitrile
2,6-dichloro-4-(trans-4-methylcyclohexyl)-benzonitrile
2,6-dichloro-4-(trans-4-ethylcyclohexyl)-benzonitrile
2,6-dichloro-4-(trans-4-propylcyclohexyl)-benzonitrile
2,6-dichloro-4-(trans-4-butylcyclohexyl)-benzonitrile
2,6-dichloro-4-(trans-4-pentylcyclohexyl)-benzonitrile
2,6-dichloro-4-(trans-4-hexylcyclohexyl)-benzonitrile
2,6-dichloro-4-(trans-4-heptylcyclohexyl)-benzonitrile
2,6-dibromo-4-(trans-4-pentylcyclohexyl)-benzonitrile
2,3,5-trifluoro-4-(trans-4-pentylcyclohexyl)-benzonitrile
2,3,6-trifluoro-4-(trans-4-pentylcyclohexyl)-benzonitrile
2,3,5,6-tetrafluoro-4-(trans-4-pentylcyclohexyl)-benzonitrile
2,6-difluoro-4-(trans-4-(trans-4-methylcyclohexyl)-cyclohexyl)-benzonitrile
2,6-difluoro-4-(trans-4-(trans-4-ethylcyclohexyl)-cyclohexyl)-benzonitrile
2,6-difluoro-4-(trans-4-(trans-4-propylcyclohexyl)-cyclohexyl)-benzonitrile
2,6-difluoro-4-(trans-4-(trans-4-butylcyclohexyl)-cyclohexyl)-benzonitrile, M 50°, C 130°
2,6-difluoro-4-(trans-4-(trans-4-pentylcyclohexyl)-cyclohexyl)-benzonitrile
2,6-difluoro-4-(trans-4-(trans-4-hexylcyclohexyl)-cyclohexyl)-benzonitrile
2,6-difluoro-4-(trans-4-(trans-4-heptylcyclohexyl)-cyclohexyl)-benzonitrile
2-chloro-6-fluoro-4-(trans-4-(trans-4-methylcyclohexyl)-cyclohexyl)-benzonitrile
2-chloro-6-fluoro-4-(trans-4-(trans-4-ethylcyclohexyl)-cyclohexyl)-benzonitrile
2-chloro-6-fluoro-4-(trans-4-(trans-4-propylcyclohexyl)-cyclohexyl)-benzonitrile
2-chloro-6-fluoro-4-(trans-4-(trans-4-butylcyclohexyl)-cyclohexyl)-benzonitrile
2-chloro-6-fluoro-4-(trans-4-(trans-4-pentylcyclohexyl)-cyclohexyl)-benzonitrile
2-chloro-6-fluoro-4-(trans-4-(trans-4-hexylcyclohexyl)-cyclohexyl)-benzonitrile
2-chloro-6-fluoro-4-(trans-4-(trans-4-heptylcyclohexyl)-cyclohexyl)-benzonitrile
2,6-dichloro-4-(trans-4-(trans-4-methylcyclohexyl)-cyclohexyl)-benzonitrile
2,6-dichloro-4-(trans-4-(trans-4-ethylcyclohexyl)-cyclohexyl)-benzonitrile
2,6-dichloro-4-(trans-4-(trans-4-propylcyclohexyl)-cyclohexyl)-benzonitrile
2,6-dichloro-4-(trans-4-(trans-4-butylcyclohexyl)-cyclohexyl)-benzonitrile
2,6-dichloro-4-(trans-4-(trans-4-pentylcyclohexyl)-cyclohexyl)-benzonitrile
2,6-dichloro-4-(trans-4-(trans-4-hexylcyclohexyl)-cyclohexyl)-benzonitrile
2,6-dichloro-4-(trans-4-(trans-4-heptylcyclohexyl)-cyclohexyl)-benzonitrile
2,6-difluoro-4-(trans-4-methyl-1,4-bicyclo[2,2,2]octyl)-benzonitrile
2,6-difluoro-4-(trans-4-ethyl-1,4-bicyclo[2,2,2]octyl)-benzonitrile
2,6-difluoro-4-(trans-4-propyl-1,4-bicyclo[2,2,2]octyl)-benzonitrile
2,6-difluoro-4-(trans-4-butyl-1,4-bicyclo[2,2,2]octyl)-benzonitrile.
2,6-difluoro-4-(trans-4-pentyl-1,4-bicyclo[2,2,2]octyl)-benzonitrile
2,6-difluoro-4-(trans-4-hexyl-1,4-bicyclo[2,2,2]octyl)-benzonitrile
2,6-difluoro-4-(trans-4-heptyl-1,4-bicyclo[2,2,2]octyl)-benzonitrile
2-chloro-6-fluoro-4-(trans-4-methyl-1,4-bicyclo[2,2,2]octyl)-benzonitrile
2-chloro-6-fluoro-4-(trans-4-ethyl-1,4-bicyclo[2,2,2]octyl)-benzonitrile
2-chloro-6-fluoro-4-(trans-4-propyl-1,4-bicyclo[2,2,2]octyl)-benzonitrile
2-chloro-4-fluoro-4-(trans-4-butyl-1,4-bicyclo[2,2,2]octyl-benzonitrile 2-chloro-6-fluoro-4-(trans-4-pentyl-1,4-bicyclo[2,2,2]octyl)-benzonitrile
2-chloro-6-fluoro-4-(trans-4-hexyl-1,4-bicyclo[2,2,2]octyl)-benzonitrile
2-chloro-6-fluoro-4-(trans-4-heptyl-1,4-bicyclo[2,2,2]octyl)-benzonitrile
2,6-dichloro-4-(trans-4-methyl-1,4-bicyclo[2,2,2]octyl)-benzonitrile
2,6-dichloro-4-(trans-4-ethyl-1,4-bicyclo[2,2,2]octyl)-benzonitrile
2,6-dichloro-4-(trans-4-propyl-1,4-bicyclo[2,2,2]octyl)-benzonitrile
2,6-dichloro-4-(trans-4-butyl-1,4-bicyclo[2,2,2]octyl)-benzonitrile
2,6-dichloro-4-(trans-4-pentyl-1,4-bicyclo[2,2,2]octyl)-benzonitrile
2,6-dichloro-4-(trans-4-hexyl-1,4-bicyclo[2,2,2]octyl)-benzonitrile
2,6-dichloro-4-(trans-4-heptyl-1,4-bicyclo[2,2,2]octyl)-benzonitrile
2,6-difluoro-4-cyano-4'-methyl biphenyl
2,6-difluoro-4-cyano-4'-ethyl biphenyl
2,6-difluoro-4-cyano-4'-propyl biphenyl
2,6-difluoro-4-cyano-4'-butyl biphenyl
2,6-difluoro-4-cyano-4'-pentyl biphenyl
2,6-difluoro-4-cyano-4'-hexyl biphenyl
2,6-difluoro-4-cyano-4'-heptyl biphenyl
2,6-difluoro-4-cyano-4'-methoxy biphenyl
2,6-difluoro-4-cyano-4'-ethoxy biphenyl
2,6-difluoro-4-cyano-4'-propoxy biphenyl
2,6-difluoro-4-cyano-4'-butoxy biphenyl
2,6-difluoro-4-cyano-4'-pentoxy biphenyl
2,6-difluoro-4-cyano-4'-hexoxy biphenyl
2,6-difluoro-4-cyano-4'-heptoxy biphenyl
2-chloro-4-cyano-6-fluoro-4'-methyl biphenyl
2-chloro-4-cyano-6-fluoro-4'-ethyl biphenyl
2-chloro-4-cyano-6-fluoro-4'-propyl biphenyl
2-chloro-4-cyano-6-fluoro-4'-butyl biphenyl
2-chloro-4-cyano-6-fluoro-4'-pentyl biphenyl
2-chloro-4-cyano-6-fluoro-4'-hexyl biphenyl
2-chloro-4-cyano-6-fluoro-4'-heptyl biphenyl
2-chloro-4-cyano-6-fluoro-4'-methoxy biphenyl
2-chloro-4-cyano-6-fluoro-4'-ethoxy biphenyl
2-chloro-4-cyano-6-fluoro-4'-propoxy biphenyl
2-chloro-4-cyano-6-fluoro-4'-butoxy biphenyl
2-chloro-4-cyano-6-fluoro-4'-pentoxy biphenyl
2-chloro-4-cyano-6-fluoro-4'-hexoxy biphenyl
2-chloro-4-cyano-6-fluoro-4'-heptoxy biphenyl
2,6-dichloro-4-cyano-4'-methyl biphenyl
2,6-dichloro-4-cyano-4'-ethyl biphenyl
2,6-dichloro-4-cyano-4'-propyl biphenyl
2,6-dichloro-4-cyano-4'-butyl biphenyl
2,6-dichloro-4-cyano-4'-pentyl biphenyl
2,6-dichloro-4-cyano-4'-hexyl biphenyl
2,6-dichloro-4-cyano-4'-heptyl biphenyl
2,6-dichloro-4-cyano-4'-methoxy biphenyl
2,6-dichloro-4-cyano-4'-ethoxy biphenyl
2,6-dichloro-4-cyano-4'-propoxy biphenyl
2,6-dichloro-4-cyano-4'-butoxy biphenyl
2,6-dichloro-4-cyano-4'-pentoxy biphenyl
2,6-dichloro-4-cyano-4'-hexoxy biphenyl
2,6-dichloro-4-cyano-4'-heptoxy biphenyl
2,6-difluoro-4-cyano-4''-propyl terphenyl
2,6-difluoro-4-cyano-4''-butyl terphenyl
2,6-difluoro-4-cyano-4''-pentyl terphenyl
2,6-difluoro-4-(trans-4-p-propylphenyl-cyclohexyl)-benzonitrile
2,6-difluoro-4-(trans-4-p-butylphenyl-cyclohexyl)-benzonitrile
2,6-difluoro-4-(trans-4-p-pentylphenyl-cyclohexyl)-benzonitrile
2,6-difluoro-4-cyano-4'-(trans-4-propylcyclohexyl)-biphenyl
2,6-difluoro-4-cyano-4'-(trans-4-butylcyclohexyl)biphenyl
2,6-difluoro-4-cyano-4'-(trans-4-pentylcyclohexyl)-biphenyl
2,6-difluoro-4-(trans-4-propylcyclohexyl)-nitrobenzene
2,6-difluoro-4-(trans-4-butylcyclohexyl)-nitrobenzene
2,6-difluoro-4-(trans-4-pentylcyclohexyl)-nitrobenzene
2,6-difluoro-4-(trans-4-(trans-4-propylcyclohexyl)-cyclohexyl)-nitrobenzene
2,6-difluoro-4-(trans-4-(trans-4-butylcyclohexyl)-cyclohexyl)-nitrobenzene
2,6-difluoro-4-(trans-4-(trans-4-pentylcyclohexyl)-cyclohexyl)-nitrobenzene
2,6-difluoro-4-nitro-4'-propyl biphenyl
2,6-difluoro-4-nitro-4'-butyl biphenyl
2,6-difluoro-4-nitro-4'-pentyl biphenyl.

EXAMPLE 2

2-(3,5-Difluoro-4-cyanophenyl)-5-butyl-1,3-dioxane is obtained analogously to Example 1 using 5-butyl-1,3-dioxane-2-carboxylic acid chloride (obtainable by reacting ethyl glyoxylate with 2-butylpropane-1,3-diol to give ethyl 5-butyl-1,3-dioxane-2-carboxylate, saponifying the latter and reacting the resulting free acid with $SOCl_2$).

The following can be obtained analogously:
2-(3,5-difluoro-4-cyanophenyl)-5-propyl-1,3-dioxane
2-(3,5-difluoro-4-cyanophenyl)-5-pentyl-1,3-dioxane
2-(3,5-dichloro-4-cyanophenyl)-5-propyl-1,3-dioxane
2-(3,5-dichloro-4-cyanophenyl)-5-butyl-1,3-dioxane
2-(3,5-dichloro-4-cyanophenyl)-5-pentyl-1,3-dioxane.

EXAMPLE 3

A Grignard solution is prepared from 28.4 g of $CH_3I$ and 4.86 g of Mg in 200 ml of ether; the bulk of the ether is replaced by 160 ml of benzene; 29.1 g of 2,6-difluoro-4-(trans-4-pentylcyclohexyl)-benzonitrile is added; and the mixture is boiled for 3 hours. It is cooled to 0°; 120 ml of cold 6N hydrochloric acid is added; the mixture is boiled for 8 hours and cooled; and working up in the usual manner gives 2,6-difluoro-4-(trans-4-pentylcyclohexyl)-acetophenone.

The following are obtained analogously by reacting the corresponding nitriles with alkylmagnesium halides, followed by hydrolysis:
2,6-difluoro-4-(trans-4-propylcyclohexyl)-acetophenone
2,6-difluoro-4-(trans-4-butylcyclohexyl)-acetophenone
2,6-difluoro-4-(trans-4-propylcyclohexyl)-propiophenone
2,6-difluoro-4-(trans-4-butylcyclohexyl)-propiophenone
2,6-difluoro-4-(trans-4-pentylcyclohexyl)-propiophenone
2,6-difluoro-4-(trans-4-propylcyclohexyl)-butyrophenone
2,6-difluoro-4-(trans-4-butylcyclohexyl)-butyrophenone
2,6-difluoro-4-(trans-4-pentylcyclohexyl)-butyrophenone
2,6-difluoro-4-(trans-4-propylcyclohexyl)-valerophenone 2,6-difluoro-4-(trans-4-butylcyclohexyl)-valerophenone
2,6-difluoro-4-(trans-4-pentylcyclohexyl)-valerophenone

EXAMPLE 4

A mixture of 30.8 g of 2,6-difluoro-4-(trans-4-pentylcyclohexyl)-acetophenone, 15 g of KOH, 25 ml of 85% hydrazine and 250 ml of diethylene glycol is heated at 100° for 1 hour. The temperature is raised slowly until the hydrazone is decomposed, the mixture is boiled for a further 4 hours and cooled and working up in the usual manner gives 1-ethyl-2,6-difluoro-4-(trans-4-pentylcyclohexyl)-benzene.

The following are obtained analogously by a Wolff-Kishner reduction of the corresponding ketones:
1-ethyl-2,6-difluoro-4-(trans-4-propylcyclohexyl)-benzene
1-ethyl-2,6-difluoro-4-(trans-4-butylcyclohexyl)-benzene
1-propyl-2,6-difluoro-4-(trans-4-propylcyclohexyl)-benzene
1-propyl-2,6-difluoro-4-(trans-4-butylcyclohexyl)-benzene
1-propyl-2,6-difluoro-4-(trans-4-pentylcyclohexyl)-benzene
1-butyl-2,6-difluoro-4-(trans-4-propylcyclohexyl)-benzene
1-butyl-2,6-difluoro-4-(trans-4-butylcyclohexyl)-benzene
1-butyl-2,6-difluoro-4-(trans-4-pentylcyclohexyl)-benzene
1-pentyl-2,6-difluoro-4-(trans-4-propylcyclohexyl)-benzene
1-pentyl-2,6-difluoro-4-(trans-4-butylcyclohexyl)-benzene
1-pentyl-2,6-difluoro-4-(trans-4-pentylcyclohexyl)-benzene.

EXAMPLE 5

(a) 31.1 g of 2,6-difluoro-4-(trans-4-pentylcyclohexyl)-nitrobenzene is dissolved in 450 ml of isopropanol and hydrogenated over 0.5 g of PtO$_2$ at 20° and under normal pressure until the calculated quantity of hydrogen has been taken up. The solution is filtered and evaporated. The resulting crude, 2,6-difluoro-4-(trans-4-pentylcyclohexyl)-aniline is dissolved in a mixture of 25 ml of concentrated sulfuric acid, 75 ml of dioxane and 75 ml of water and is diazotized at 3° to 6° with a solution of 8 g of NaNO$_2$ in 15 ml of water. The mixture thus obtained is introduced in portions while stirring into 500 ml of boiling water. The mixture is boiled for a further 30 minutes and cooled and the resulting 2,6-difluoro-4-(trans-4-pentylcyclohexyl)-phenol is filtered off and dissolved in 250 ml of 1N sodium hydroxide solution. 12.6 g of dimethyl sulfate is added in portions and the mixture is then heated at 100° for 1 hour. Cooling and working up in the usual manner gives 2,6-difluoro-4-(trans-4-pentylcyclohexyl)-anisole.

(b) A mixture of 28.2 g of 2,6-difluoro-4-(trans-4-pentylcyclohexyl)-phenol, 6.9 g of K$_2$CO$_3$, 25 g of hexyl iodide and 250 ml of dimethylformamide is heated at 80° for 16 hours, while stirring, and is then cooled and worked up in the usual manner. This gives 2,6-difluoro-4-(trans-4-pentylcyclohexyl)-1-hexoxybenzene.

The following:
2,6-difluoro-4-(trans-4-propylcyclohexyl)-1-methoxybenzene
2,6-difluoro-4-(trans-4-propylcyclohexyl)-1-ethoxybenzene
2,6-difluoro-4-(trans-4-propylcyclohexyl)-1-propoxybenzene
2,6-difluoro-4-(trans-4-propylcyclohexyl)-1-butoxybenzene
2,6-difluoro-4-(trans-4-propylcyclohexyl)-1-pentoxybenzene
2,6-difluoro-4-(trans-4-butylcyclohexyl)-1-methoxybenzene
2,6-difluoro-4-(trans-4-butylcyclohexyl)-1-ethoxybenzene
2,6-difluoro-4-(trans-4-butylcyclohexyl)-1-propoxybenzene
2,6-difluoro-4-(trans-4-butylcyclohexyl)-1-butoxybenzene
2,6-difluoro-4-(trans-4-butylcyclohexyl)-1-pentoxybenzene
2,6-difluoro-4-(trans-4-pentylcyclohexyl)-1-methoxybenzene
2,6-difluoro-4-(trans-4-pentylcyclohexyl)-1-ethoxybenzene
2,6-difluoro-4-(trans-4-pentylcyclohexyl)-1-propoxybenzene
2,6-difluoro-4-(trans-4-pentylcyclohexyl)-1-butoxybenzene
2,6-difluoro-4-(trans-4-pentylcyclohexyl)-1-pentoxybenzene
are obtained analogously by etherification via:
2,6-difluoro-4-(trans-4-propylcyclohexyl)-aniline,
2,6-difluoro-4-(trans-4-butylcyclohexyl)-aniline or
2,6-difluoro-4-(trans-4-pentylcyclohexyl)-aniline,
respectively, and:
2,6-difluoro-4-(trans-4-propylcyclohexyl)-phenol,
2,6-difluoro-4-(trans-4-butylcyclohexyl)-phenol or
2,6-difluoro-4-(trans-4-pentylcyclohexyl)-phenol,
respectively.

EXAMPLE 6

8 g of acetyl chloride is added to a solution of 28.2 g of 2,6-difluoro-4-(trans-4-pentylcyclohexyl)-phenol and 20 ml of pyridine in 300 ml of toluene, and the mixture is heated at 80° for 1 hour. Cooling and working up in the usual manner gives 2,6-difluoro-4-(trans-4-pentylcyclohexyl)-phenyl acetate.

The following are obtained analogously by esterifying the corresponding phenols:
2,6-difluoro-4-(trans-4-propylcyclohexyl)-phenyl acetate
2,6-difluoro-4-(trans-4-butylcyclohexyl)-phenyl acetate.

EXAMPLE 7

(a) A solution of 10 g of 2,6-difluoro-4-(trans-4-pentylcyclohexyl)-benzonitrile and 20 g of KOH in 40 ml of water and 160 ml of ethanol is boiled for 16 hours, cooled and worked up in the usual manner to give 2,6-difluoro-4-(trans-4-pentylcyclohexyl)-benzoic acid.

(b) 10 g of 2,6-difluoro-4-(trans-4-pentylcyclohexyl)-benzoic acid is allowed to stand with 200 ml of methanolic hydrochloric acid for 24 hours at 20°, and the mixture is evaporated to give methyl 2,6-difluoro-4-(trans-4-pentylcyclohexyl)-benzoate.

(c) 31 g of 2,6-difluoro-4-(trans-4-pentylcyclohexyl)-benzoic acid is boiled for 1 hour with 24 g of SOCl$_2$, the mixture is evaporated; the resulting crude acid chloride is dissolved in 150 ml of toluene; 7.9 g of pyridine and 6 g of propanol is added; and the mixture is boiled for 2 hours. The mixture is cooled and worked up in the usual manner. This gives propyl 2,6-difluoro-4-(trans-4-pentylcyclohexyl)-benzoate.

The following are obtained analogously by esterification:

p-propylphenyl 2,6-difluoro-4-(trans-4-pentylcyclohexyl)-benzoate
p-methoxyphenyl 2,6-difluoro-4-(trans-4-pentylcyclohexyl)-benzoate
p-ethoxyphenyl 2,6-difluoro-4-(trans-4-pentylcyclohexyl)-benzoate
p-dodecyloxyphenyl 2,6-difluoro-4-(trans-4-pentylcyclohexyl)-benzoate
p-cyanophenyl 2,6-difluoro-4-(trans-4-pentylcyclohexyl)-benzoate
trans-4-propylcyclohexyl 2,6-difluoro-4-(trans-4-pentylcyclohexyl)-benzoate.

The following are examples of dielectrics according to this invention containing at least one compound of the Formula I:

EXAMPLE A

A mixture of
24% of 2,6-difluoro-4-(trans-4-pentylcyclohexyl)-benzonitrile,
36% of p-(trans-4-pentylcyclohexyl)-benzonitrile,
25% of p-(trans-4-heptylcyclohexyl)-benzonitrile and
15% of 4'-(trans-4-pentylcyclohexyl)-biphenyl-4-carbonitrile
has M. −5° and C. 57°.

EXAMPLE B

A mixture of:
17% of 2,6-difluoro-4-(trans-4-pentylcyclohexyl)-benzonitrile,
23% of 2,6-difluoro-4-(4-pentylbicyclo[2,2,2]oct-1-yl)-benzonitrile,
16% of trans-1-(p-ethoxyphenyl)-4-propylcyclohexane,
12% of trans-1-(p-butoxyphenyl)-4-propylcyclohexane,
22% of 4-ethyl-4'-(trans-4-pentylcyclohexyl)-biphenyl and
10% of 4-(trans-4-pentylcyclohexyl)-4'-(trans-4-propylcyclohexyl)-biphenyl
has M. −10° and C. 78°.

EXAMPLE C

A mixture of
26% of 2,6-difluoro-4-(4-pentylbicyclo[2,2,2]oct-1-yl)-benzonitrile,
30% of 4-pentyl-4'-cyanobiphenyl,
14% of 4-heptyl-4'-cyanobiphenyl,
6% of 4''-pentyl-4-cyanoterphenyl,
13% of p-ethoxyphenyl trans-4-propylcyclohexanecarboxylate and
11% of 2-p-cyanophenyl-5-pentyl-1,3-dioxane
has M. −12° and C. 58°.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid-crystal dielectric useful in electrooptical display elements comprising at least two liquid-crystalline components, wherein at least one component is a polyhalogenoaromatic compound of the formula

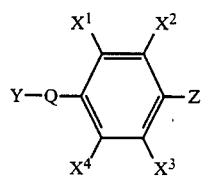

wherein Y and Z are each independently alkyl, alkoxy or alkanoyl each of 1 to 12 C atoms, $-COOR^1$, $-O-CO-R^1$, CN, or $NO_2$; Q is one or two identical or different groups selected from Ph, Cy, or 1,4-bicyclo[2,2,2]octylene; $X^1$ to $X^4$ are each independently H, F, Cl or Br; $R^1$ is alkyl of 1 to 4 C atoms, $Ph-R^2$ or $Cy-R^2$; $R^2$ is alkyl or alkoxy each of 1-12 C atoms, or CN; Ph is 1,4-phenylene; and Cy is 1,4-cyclohexylene; with the proviso that not more than one of $X^1$ and $X^2$ and not more than one of $X^3$ and $X^4$ is hydrogen.

2. A liquid crystal dielectric of claim 1, wherein said at least one component is of the formula

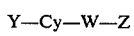

wherein W is $2-X^2-3-X^1-5-X^4-6-X^3$-1,4-phenylene.

3. A liquid crystal dielectric of claim 1, wherein said at least one component is of the formula
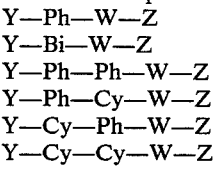

wherein W is $2-X^2-3-X^1-5-X^4-6-X^3$-1,4-phenylene, Bi is 1,4-bicyclo[2,2,2]octylene.

4. A liquid crystal dielectric of claim 1, wherein said at least one component is of the formula
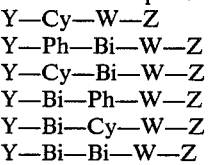

wherein W is $2-X^2-3-X^1-5-X^4-6-X^3$-1,4-phenylene, and Bi is 1,4-bicyclo[2,2,2]octylene.

5. A liquid crystalline dielectric of claim 1, wherein in said at least one component, the alkyl portion of all groups is straight chained.

6. A liquid crystalline dielectric of claim 1, wherein in said at least one component, the substituents on all cyclohexylene groups are trans relative to each other.

7. A liquid crystalline dielectric of claim 1, wherein in said at least one component, the alkyl portion of all groups is of 1-6 C atoms.

8. A liquid crystalline dielectric of claim 1, wherein said at least one component contains only one branched alkyl portion which contains only one chain branching.

9. A liquid crystal dielectric of claim 1, wherein in said at least one component, Y is alkyl.

10. A liquid crystalline dielectric of claim 1, wherein in said at least one component, Z is CN or $NO_2$.

11. A liquid crystalline dielectric of claim 1, wherein in said at least one component, the $X^1-X^4$-substituted benzene ring is 2,6-dihalogeno-1,4-phenylene.

12. A liquid crystalline dielectric of claim 1, wherein in said at least one component, at least one of $X^1$–$X^4$ is F.

13. A liquid crystalline dielectric of claim 1, wherein in said at least one component the $X^1$–$X^4$-substituted benzene ring is 2,6-difluoro-1,4-phenylene, 2-chloro-6-fluoro-1,4-phenylene or 2,6-chloro-1,4-phenylene.

14. A liquid crystalline dielectric of claim 1, wherein in said at least one component, $R^1$ is linear alkyl of 1-4 C-atoms, Ph—$R^2$ or Cy—$R^2$.

15. A liquid crystalline dielectric of claim 1, wherein in said at least one component, $R^2$ is alkyl.

16. A dielectric of claim 1 comprising 2–15 liquid crystalline components.

17. A dielectric of claim 1 wherein the amount of said polyhalogenoaromatic compound is 0.1–30 wt. %.

18. In an electrooptical display element comprising a liquid-crystal cell having a liquid-crystal dielectric, the improvement wherein the dielectric is that of claim 1.

19. A liquid crystalline dielectric of claim 1, wherein in said at least one component, at least one of $X^1$–$X^4$ is Cl.

20. A liquid crystalline dielectric of claim 1, wherein in said at least one component, at least one of $X^1$–$X^4$ is Br.

21. A liquid crystalline dielectric of claim 1, wherein in said at least one component, at least one of $X^1$–$X^4$ is H.

* * * * *